(12) United States Patent
Ortiz et al.

(10) Patent No.: US 7,575,144 B2
(45) Date of Patent: Aug. 18, 2009

(54) SURGICAL FASTENER AND CUTTER WITH SINGLE CABLE ACTUATOR

(75) Inventors: Mark S. Ortiz, Milford, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 134 days.

(21) Appl. No.: 11/277,320

(22) Filed: Mar. 23, 2006

(65) Prior Publication Data

US 2007/0175947 A1    Aug. 2, 2007

Related U.S. Application Data

(63) Continuation-in-part of application No. 11/344,021, filed on Jan. 31, 2006, now Pat. No. 7,464,849.

(51) Int. Cl.
*A61B 17/10* (2006.01)
(52) U.S. Cl. .................. 227/175.1; 227/19; 227/179.1
(58) Field of Classification Search .............. 227/178.1, 227/179.1, 19, 181.1
See application file for complete search history.

(56) References Cited

U.S. PATENT DOCUMENTS

| | | | |
|---|---|---|---|
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,819,100 A | 6/1974 | Noiles et al. |
| 3,892,228 A | 7/1975 | Mitsui |
| 3,894,174 A | 7/1975 | Cartun |
| 3,940,844 A | 3/1976 | Colby et al. |
| 4,213,562 A | 7/1980 | Garrett et al. |
| 4,331,277 A | 5/1982 | Green |
| 4,349,028 A | 9/1982 | Green |
| 4,383,634 A | 5/1983 | Green |
| 4,402,445 A | 9/1983 | Green |
| 4,415,112 A | 11/1983 | Green |
| 4,454,887 A | 6/1984 | Kruger |

(Continued)

FOREIGN PATENT DOCUMENTS

CA    245894    1/1925

(Continued)

OTHER PUBLICATIONS

Frederick Van Meer, et al., "A Disposable Plastic Compact Wrist for Smart Minimally Invasive Surgical Tools," LAAS/CNRS (Aug. 2005).

(Continued)

*Primary Examiner*—Brian D Nash
(74) *Attorney, Agent, or Firm*—Nutter McClennen & Fish LLP

(57) ABSTRACT

Methods and devices are provided for controlling rotation and actuation of an end effector on a surgical fastening device. In an exemplary embodiment, a single cable actuator is provided and is movable between a first position, in which it is effective to rotate an end effector without actuating (i.e., closing and firing) the end effector, and a second position, in which it is effective to actuate the end effector without rotating the end effector. The single cable can also be effective to close opposed jaws of the end effector.

16 Claims, 12 Drawing Sheets

U.S. PATENT DOCUMENTS

| | | | |
|---|---|---|---|
| 4,475,679 A | 10/1984 | Fleury, Jr. | |
| 4,500,024 A | 2/1985 | DiGiovanni et al. | |
| 4,520,817 A | 6/1985 | Green | |
| 4,522,327 A | 6/1985 | Korthoff et al. | |
| 4,526,174 A | 7/1985 | Froehlich | |
| 4,527,724 A | 7/1985 | Chow et al. | |
| 4,530,453 A | 7/1985 | Green | |
| 4,566,620 A | 1/1986 | Green et al. | |
| 4,573,622 A | 3/1986 | Green et al. | |
| 4,580,712 A | 4/1986 | Green | |
| 4,605,001 A | 8/1986 | Rothfuss et al. | |
| 4,606,343 A | 8/1986 | Conta et al. | |
| 4,608,981 A | 9/1986 | Rothfuss et al. | |
| 4,610,383 A | 9/1986 | Rothfuss et al. | |
| 4,629,107 A | 12/1986 | Fedotov et al. | |
| 4,671,445 A | 6/1987 | Barker et al. | |
| 4,709,120 A | 11/1987 | Pearson | |
| 4,715,520 A | 12/1987 | Roehr, Jr. et al. | |
| 4,728,020 A | 3/1988 | Green et al. | |
| 4,728,876 A | 3/1988 | Mongeon et al. | |
| 4,729,260 A | 3/1988 | Dudden | |
| 4,754,909 A | 7/1988 | Barker et al. | |
| 4,767,044 A | 8/1988 | Green | |
| 4,790,225 A | 12/1988 | Moody et al. | |
| 4,869,414 A | 9/1989 | Green et al. | |
| 4,869,415 A | 9/1989 | Fox | |
| 4,880,015 A | 11/1989 | Nierman | |
| 4,892,244 A | 1/1990 | Fox et al. | |
| 4,938,408 A | 7/1990 | Bedi et al. | |
| 4,941,623 A | 7/1990 | Pruitt | |
| 4,944,443 A | 7/1990 | Oddsen et al. | |
| 4,955,959 A | 9/1990 | Tompkins et al. | |
| 4,978,049 A | 12/1990 | Green | |
| 5,027,834 A | 7/1991 | Pruitt | |
| 5,031,814 A | 7/1991 | Tompkins et al. | |
| 5,040,715 A * | 8/1991 | Green et al. | 227/176.1 |
| 5,084,057 A * | 1/1992 | Green et al. | 606/142 |
| 5,088,979 A | 2/1992 | Filipi et al. | |
| 5,100,420 A * | 3/1992 | Green et al. | 606/143 |
| 5,211,649 A | 5/1993 | Kohler et al. | |
| 5,259,366 A | 11/1993 | Reydel et al. | |
| RE34,519 E | 1/1994 | Fox et al. | |
| 5,381,782 A | 1/1995 | DeLaRama et al. | |
| 5,383,880 A | 1/1995 | Hooven et al. | |
| 5,431,322 A | 7/1995 | Green et al. | |
| 5,433,721 A | 7/1995 | Hooven et al. | |
| 5,465,894 A | 11/1995 | Clark et al. | |
| 5,472,132 A | 12/1995 | Savage et al. | |
| 5,474,566 A | 12/1995 | Alesi et al. | |
| 5,476,206 A | 12/1995 | Green et al. | |
| 5,476,479 A | 12/1995 | Green et al. | |
| 5,478,003 A | 12/1995 | Green et al. | |
| 5,480,089 A | 1/1996 | Blewett | |
| 5,480,409 A | 1/1996 | Riza | |
| 5,482,197 A | 1/1996 | Green et al. | |
| 5,484,095 A | 1/1996 | Green et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,489,256 A | 2/1996 | Adair | |
| 5,497,933 A | 3/1996 | DeFonzo et al. | |
| 5,503,320 A | 4/1996 | Webster et al. | |
| 5,503,638 A | 4/1996 | Cooper et al. | |
| 5,509,596 A | 4/1996 | Green et al. | |
| 5,518,163 A | 5/1996 | Hooven | |
| 5,518,164 A | 5/1996 | Hooven | |
| 5,522,817 A | 6/1996 | Sander et al. | |
| 5,527,320 A | 6/1996 | Carruthers et al. | |
| 5,529,235 A | 6/1996 | Boiarski et al. | |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,547,117 A | 8/1996 | Hamblin et al. |
| 5,549,628 A | 8/1996 | Cooper et al. |
| 5,553,675 A | 9/1996 | Pitzen et al. |
| 5,554,169 A | 9/1996 | Green et al. |
| 5,558,665 A | 9/1996 | Kieturakis |
| 5,560,532 A | 10/1996 | DeFonzo et al. |
| 5,562,239 A | 10/1996 | Boiarski et al. |
| 5,562,241 A | 10/1996 | Knodel et al. |
| 5,564,615 A | 10/1996 | Bishop et al. |
| 5,571,116 A | 11/1996 | Bolanos et al. |
| 5,574,431 A | 11/1996 | McKeown et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,782 A | 5/1997 | Adair |
| 5,632,432 A | 5/1997 | Schulze et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,651,491 A | 7/1997 | Heaton et al. |
| 5,653,374 A | 8/1997 | Young et al. |
| 5,657,921 A | 8/1997 | Young et al. |
| 5,658,300 A | 8/1997 | Bito et al. |
| 5,662,258 A | 9/1997 | Knodel et al. |
| 5,662,662 A | 9/1997 | Bishop et al. |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,697,543 A | 12/1997 | Burdorff |
| 5,700,270 A | 12/1997 | Peyser et al. |
| 5,702,408 A | 12/1997 | Wales et al. |
| 5,704,534 A | 1/1998 | Huitema et al. |

| Patent No. | Date | Inventor |
|---|---|---|
| 5,706,997 A | 1/1998 | Green et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,758,814 A | 6/1998 | Gallagher et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,785,232 A | 7/1998 | Vidal et al. |
| 5,787,897 A | 8/1998 | Kieturakis |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,807,393 A | 9/1998 | Williamson, IV et al. |
| 5,809,441 A | 9/1998 | McKee |
| 5,810,811 A | 9/1998 | Yates et al. |
| 5,813,813 A | 9/1998 | Daum et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,690 A | 11/1998 | Yates et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,132 A | 12/1998 | Ilvento |
| 5,855,311 A | 1/1999 | Hamblin et al. |
| 5,865,361 A | 2/1999 | Milliman et al. |
| 5,871,135 A | 2/1999 | Williamson IV et al. |
| 5,873,885 A | 2/1999 | Weidenbenner |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,911,353 A | 6/1999 | Bolanos et al. |
| 5,915,616 A | 6/1999 | Viola et al. |
| 5,918,791 A | 7/1999 | Sorrentino et al. |
| 5,931,853 A | 8/1999 | McEwen et al. |
| 5,938,667 A | 8/1999 | Peyser et al. |
| 5,941,442 A | 8/1999 | Geiste et al. |
| 5,951,552 A | 9/1999 | Long et al. |
| 5,951,574 A | 9/1999 | Stefanchik et al. |
| 5,954,259 A | 9/1999 | Viola et al. |
| 5,988,479 A | 11/1999 | Palmer |
| 6,010,054 A | 1/2000 | Johnson et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,032,849 A | 3/2000 | Mastri et al. |
| 6,071,233 A | 6/2000 | Ishikawa et al. |
| 6,079,606 A | 6/2000 | Milliman et al. |
| 6,082,577 A | 7/2000 | Coates et al. |
| 6,083,234 A | 7/2000 | Nicholas et al. |
| 6,086,600 A | 7/2000 | Kortenbach |
| 6,102,271 A | 8/2000 | Longo et al. |
| 6,109,500 A | 8/2000 | Alli et al. |
| 6,126,670 A | 10/2000 | Walker et al. |
| 6,131,789 A | 10/2000 | Schulze et al. |
| 6,155,473 A | 12/2000 | Tompkins et al. |
| 6,156,056 A | 12/2000 | Kearns et al. |
| 6,159,146 A | 12/2000 | El Gazayerli |
| 6,162,208 A | 12/2000 | Hipps |
| 6,179,776 B1 | 1/2001 | Adams et al. |
| 6,202,914 B1 | 3/2001 | Geiste et al. |
| 6,223,835 B1 | 5/2001 | Habedank et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,309,403 B1 | 10/2001 | Minor et al. |
| 6,315,184 B1 | 11/2001 | Whitman |
| 6,320,123 B1 | 11/2001 | Reimers |
| 6,325,810 B1 | 12/2001 | Hamilton et al. |
| 6,330,965 B1 | 12/2001 | Milliman et al. |
| 6,352,503 B1 | 3/2002 | Matsui et al. |
| 6,358,224 B1 | 3/2002 | Tims et al. |
| 6,416,486 B1 | 7/2002 | Wampler |
| 6,443,973 B1 | 9/2002 | Whitman |
| 6,488,197 B1 | 12/2002 | Whitman |
| 6,491,201 B1 | 12/2002 | Whitman |
| 6,492,785 B1 | 12/2002 | Kasten et al. |
| 6,503,257 B2 | 1/2003 | Grant et al. |
| 6,505,768 B2 | 1/2003 | Whitman |
| 6,511,468 B1 | 1/2003 | Cragg et al. |
| 6,522,101 B2 | 2/2003 | Malackowski |
| 6,550,546 B2 | 4/2003 | Thurler et al. |
| 6,569,085 B2 | 5/2003 | Kortenbach et al. |
| 6,592,597 B2 | 7/2003 | Grant et al. |
| 6,602,252 B2 | 8/2003 | Mollenauer |
| 6,619,529 B2 | 9/2003 | Green et al. |
| 6,620,166 B1 | 9/2003 | Wenstrom, Jr. et al. |
| 6,629,988 B2 | 10/2003 | Weadock |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,705,503 B1 | 3/2004 | Pedicini et al. |
| 6,716,232 B1 | 4/2004 | Vidal et al. |
| 6,716,233 B1 | 4/2004 | Whitman |
| 6,740,030 B2 | 5/2004 | Martone et al. |
| 6,752,816 B2 | 6/2004 | Culp et al. |
| 6,755,338 B2 | 6/2004 | Hahnen et al. |
| 6,761,685 B2 | 7/2004 | Adams et al. |
| 6,773,438 B1 | 8/2004 | Knodel et al. |
| 6,786,382 B1 | 9/2004 | Hoffman |
| 6,786,864 B2 | 9/2004 | Matsuura et al. |
| 6,790,173 B2 | 9/2004 | Saadat et al. |
| 6,793,652 B1 | 9/2004 | Whitman et al. |
| 6,805,273 B2 | 10/2004 | Bilotti et al. |
| 6,806,808 B2 | 10/2004 | Watters et al. |
| 6,814,741 B2 | 11/2004 | Bowman et al. |
| 6,817,509 B2 | 11/2004 | Geiste et al. |
| 6,821,273 B2 | 11/2004 | Mollenauer |
| 6,828,902 B2 | 12/2004 | Casden |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| 6,846,307 B2 | 1/2005 | Whitman et al. |

| Patent No. | Date | Inventor |
|---|---|---|
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,878,106 B1 | 4/2005 | Herrmann et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,984,203 B2 | 1/2006 | Tartaglia et al. |
| 6,986,451 B1 | 1/2006 | Mastri et al. |
| 6,988,649 B2 | 1/2006 | Shelton, IV et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,029,435 B2 | 4/2006 | Nakao |
| 7,032,798 B2 | 4/2006 | Whitman et al. |
| 7,036,680 B1 | 5/2006 | Flannery |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,059,508 B2 | 6/2006 | Shelton, IV et al. |
| 7,066,944 B2 | 6/2006 | Laufer et al. |
| 7,070,559 B2 | 7/2006 | Adams et al. |
| 7,077,856 B2 | 7/2006 | Whitman |
| 7,083,075 B2 | 8/2006 | Swayze et al. |
| 7,090,673 B2 | 8/2006 | Dycus et al. |
| 7,090,684 B2 | 8/2006 | McGuckin, Jr. et al. |
| 7,097,089 B2 | 8/2006 | Marczyk |
| 7,098,794 B2 | 8/2006 | Lindsay et al. |
| 7,111,769 B2 | 9/2006 | Wales et al. |
| 7,114,642 B2 | 10/2006 | Whitman |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,159,750 B2 | 1/2007 | Racenet et al. |
| 7,168,604 B2 | 1/2007 | Milliman et al. |
| 7,188,758 B2 | 3/2007 | Viola et al. |
| 7,210,609 B2 | 5/2007 | Leiboff et |
| 7,225,964 B2 | 6/2007 | Mastri et al. |
| 7,246,734 B2 | 7/2007 | Shelton, IV |
| 7,258,262 B2 | 8/2007 | Mastri et al. |
| 7,338,513 B2 | 3/2008 | Lee et al. |
| 2002/0049454 A1 | 4/2002 | Whitman et al. |
| 2002/0117534 A1 | 8/2002 | Green et al. |
| 2002/0143078 A1 | 10/2002 | Awokola et al. |
| 2002/0165541 A1 | 11/2002 | Whitman |
| 2003/0105478 A1 | 6/2003 | Whitman et al. |
| 2003/0130677 A1 | 7/2003 | Whitman et al. |
| 2003/0195387 A1 | 10/2003 | Kortenbach et al. |
| 2003/0216778 A1 | 11/2003 | Weadock |
| 2003/0233066 A1 | 12/2003 | Ewers et al. |
| 2004/0028502 A1 | 2/2004 | Cummins |
| 2004/0068161 A1 | 4/2004 | Couvillon |
| 2004/0094597 A1 | 5/2004 | Whitman et al. |
| 2004/0097987 A1 | 5/2004 | Pugsley et al. |
| 2004/0108357 A1 | 6/2004 | Milliman et al. |
| 2004/0111081 A1 | 6/2004 | Whitman et al. |
| 2004/0116952 A1 | 6/2004 | Sakurai et al. |
| 2004/0122471 A1 | 6/2004 | Toby et al. |
| 2004/0133075 A1 | 7/2004 | Motoki et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0230096 A1 | 11/2004 | Stefanchik et al. |
| 2004/0230097 A1 | 11/2004 | Stefanchik et al. |
| 2004/0230214 A1 | 11/2004 | Donofrio et al. |
| 2004/0232195 A1* | 11/2004 | Shelton et al. ............ 227/175.1 |
| 2004/0232196 A1* | 11/2004 | Shelton et al. ............ 227/175.1 |
| 2004/0232199 A1 | 11/2004 | Shelton et al. |
| 2004/0232201 A1 | 11/2004 | Wenchell et al. |
| 2004/0236316 A1 | 11/2004 | Danitz et al. |
| 2004/0243151 A1 | 12/2004 | Demmy et al. |
| 2004/0243176 A1 | 12/2004 | Hahnen et al. |
| 2005/0006429 A1* | 1/2005 | Wales et al. ............... 227/175.1 |
| 2005/0006434 A1 | 1/2005 | Wales et al. |
| 2005/0021026 A1 | 1/2005 | Baily |
| 2005/0023324 A1 | 2/2005 | Doll et al. |
| 2005/0033357 A1 | 2/2005 | Braun |
| 2005/0070925 A1 | 3/2005 | Shelton et al. |
| 2005/0070958 A1 | 3/2005 | Swayze et al. |
| 2005/0072827 A1 | 4/2005 | Mollenauer |
| 2005/0096694 A1 | 5/2005 | Lee |
| 2005/0103819 A1 | 5/2005 | Racenet et al. |
| 2005/0107824 A1 | 5/2005 | Hillstead et al. |
| 2005/0119525 A1 | 6/2005 | Takemoto |
| 2005/0119669 A1* | 6/2005 | Demmy ........................ 606/139 |
| 2005/0124855 A1 | 6/2005 | Jaffe et al. |
| 2005/0125009 A1 | 6/2005 | Perry et al. |
| 2005/0131163 A1 | 6/2005 | Rhine et al. |
| 2005/0131164 A1 | 6/2005 | Lenges et al. |
| 2005/0131173 A1 | 6/2005 | McDaniel et al. |
| 2005/0131211 A1 | 6/2005 | Bayley et al. |
| 2005/0131212 A1 | 6/2005 | Sieg et al. |
| 2005/0131390 A1 | 6/2005 | Heinrich et al. |
| 2005/0137423 A1 | 6/2005 | Oikawa et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0145671 A1 | 7/2005 | Viola |
| 2005/0149067 A1 | 7/2005 | Takemoto et al. |
| 2005/0152416 A1 | 7/2005 | Chang |
| 2005/0154258 A1 | 7/2005 | Tartaglia et al. |
| 2005/0165415 A1 | 7/2005 | Wales |
| 2005/0165419 A1 | 7/2005 | Sauer et al. |
| 2005/0171522 A1 | 8/2005 | Christopherson |
| 2005/0173490 A1 | 8/2005 | Shelton |
| 2005/0177181 A1 | 8/2005 | Kagan et al. |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0203550 A1 | 9/2005 | Laufer et al. |
| 2005/0216055 A1 | 9/2005 | Scirica et al. |
| 2005/0230453 A1 | 10/2005 | Viola |
| 2005/0234297 A1 | 10/2005 | Devierre et al. |
| 2005/0263562 A1 | 12/2005 | Shelton et al. |
| 2005/0263563 A1 | 12/2005 | Racenet et al. |
| 2005/0274768 A1 | 12/2005 | Cummins et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020287 A1 | 1/2006 | Lee et al. |
| 2006/0025811 A1 | 2/2006 | Shelton |
| 2006/0025812 A1 | 2/2006 | Shelton |
| 2006/0025813 A1 | 2/2006 | Shelton et al. |
| 2006/0025816 A1 | 2/2006 | Shelton |
| 2006/0047303 A1 | 3/2006 | Ortiz et al. |
| 2006/0047308 A1 | 3/2006 | Ortiz et al. |
| 2006/0049229 A1 | 3/2006 | Milliman et al. |
| 2006/0060630 A1 | 3/2006 | Shelton et al. |
| 2006/0079735 A1 | 4/2006 | Martone et al. |

| Publication | Date | Inventors | | Patent | Date |
|---|---|---|---|---|---|
| 2006/0087442 A1 | 4/2006 | Smith et al. | DE | 20112837 | 10/2001 |
| 2006/0097026 A1 | 5/2006 | Shelton | DE | 10314072 | 10/2004 |
| 2006/0100643 A1 | 5/2006 | Laufer et al. | DE | 69328576 | 8/2008 |
| 2006/0108393 A1 | 5/2006 | Heinrich et al. | EA | 0 634 144 A1 | 1/1995 |
| 2006/0122636 A1 | 6/2006 | Bailly et al. | EP | 0878169 | 11/1970 |
| 2006/0142772 A1 | 6/2006 | Ralph et al. | EP | 0033548 | 8/1981 |
| 2006/0151567 A1 | 7/2006 | Roy | EP | 0122046 | 10/1984 |
| 2006/0190028 A1 | 8/2006 | Wales et al. | EP | 0392547 | 10/1990 |
| 2006/0190029 A1 | 8/2006 | Wales | EP | 0484677 | 5/1992 |
| 2006/0190031 A1 | 8/2006 | Wales et al. | EP | 0 552 050 A2 | 1/1993 |
| 2006/0226196 A1 | 10/2006 | Hueil et al. | EP | 0537572 | 4/1993 |
| 2006/0229665 A1 | 10/2006 | Wales et al. | EP | 0541987 | 5/1993 |
| 2006/0278681 A1 | 12/2006 | Viola et al. | EP | 0 552 423 | 7/1993 |
| 2006/0278880 A1 | 12/2006 | Lee et al. | EP | 0592244 | 4/1994 |
| 2006/0289602 A1 | 12/2006 | Wales et al. | EP | 0593920 | 4/1994 |
| 2007/0027469 A1 | 2/2007 | Smith et al. | EP | 0600182 A | 6/1994 |
| 2007/0034666 A1 | 2/2007 | Holsten et al. | EP | 0603472 | 6/1994 |
| 2007/0034668 A1 | 2/2007 | Holsten et al. | EP | 0625335 | 11/1994 |
| 2007/0045379 A1 | 3/2007 | Shelton | EP | 0630612 | 12/1994 |
| 2007/0073340 A1 | 3/2007 | Shelton et al. | EP | 0 646 356 | 4/1995 |
| 2007/0075114 A1 | 4/2007 | Shelton et al. | EP | 0646357 | 4/1995 |
| 2007/0083234 A1 | 4/2007 | Shelton et al. | EP | 0648476 | 4/1995 |
| 2007/0084897 A1 | 4/2007 | Shelton et al. | EP | 0656188 | 6/1995 |
| 2007/0102452 A1 | 5/2007 | Shelton et al. | EP | 0667119 | 8/1995 |
| 2007/0102453 A1 | 5/2007 | Morgan et al. | EP | 0669104 | 8/1995 |
| 2007/0102472 A1 | 5/2007 | Shelton | EP | 0679367 | 11/1995 |
| 2007/0102473 A1 | 5/2007 | Shelton et al. | EP | 0685204 | 12/1995 |
| 2007/0102474 A1 | 5/2007 | Shelton et al. | EP | 0699418 | 3/1996 |
| 2007/0102475 A1 | 5/2007 | Ortiz et al. | EP | 0702937 | 3/1996 |
| 2007/0102476 A1 | 5/2007 | Shelton et al. | EP | 0 705 570 B1 | 4/1996 |
| 2007/0106317 A1 | 5/2007 | Shelton et al. | EP | 0705571 | 4/1996 |
| 2007/0158358 A1 | 7/2007 | Mason et al. | EP | 0760230 | 3/1997 |
| 2007/0170225 A1 | 7/2007 | Shelton et al. | EP | 0770355 | 5/1997 |
| 2007/0175949 A1 | 8/2007 | Shelton et al. | EP | 0813843 | 12/1997 |
| 2007/0175950 A1 | 8/2007 | Shelton et al. | EP | 0829235 | 3/1998 |
| 2007/0175951 A1 | 8/2007 | Shelton et al. | EP | 0872213 | 10/1998 |
| 2007/0175952 A1 | 8/2007 | Shelton et al. | EP | 0 880 338 | 12/1998 |
| 2007/0175953 A1 | 8/2007 | Shelton et al. | EP | 0888749 | 1/1999 |
| 2007/0175955 A1 | 8/2007 | Shelton et al. | EP | 0908152 | 4/1999 |
| 2007/0175956 A1 | 8/2007 | Swayze et al. | EP | 0 552 050 B1 | 5/2000 |
| 2007/0175957 A1 | 8/2007 | Shelton et al. | EP | 1045672 | 10/2000 |
| 2007/0175958 A1 | 8/2007 | Shelton et al. | EP | 1064883 | 1/2001 |
| 2007/0175959 A1 | 8/2007 | Shelton et al. | EP | 0639349 | 2/2001 |
| 2007/0175960 A1 | 8/2007 | Shelton et al. | EP | 1086713 | 3/2001 |
| 2007/0175962 A1 | 8/2007 | Shelton et al. | EP | 1090592 | 4/2001 |
| 2007/0175964 A1 | 8/2007 | Shelton et al. | EP | 1129665 | 9/2001 |
| 2007/0179476 A1 | 8/2007 | Shelton et al. | EP | 1238634 | 9/2002 |
| 2007/0181632 A1 | 8/2007 | Milliman | EP | 1256317 | 11/2002 |
| 2007/0194079 A1 | 8/2007 | Hueil et al. | EP | 1256318 | 11/2002 |
| 2007/0194080 A1 | 8/2007 | Swayze et al. | EP | 1 284 120 | 2/2003 |
| 2007/0194081 A1 | 8/2007 | Hueil et al. | EP | 1300117 | 4/2003 |
| 2007/0194082 A1 | 8/2007 | Morgan et al. | EP | 1382303 | 1/2004 |
| 2007/0233053 A1 | 10/2007 | Shelton et al. | EP | 1 400 214 | 3/2004 |
| 2007/0262116 A1 | 11/2007 | Hueil et al. | EP | 1 402 837 | 3/2004 |
| 2007/0295780 A1 | 12/2007 | Shelton et al. | EP | 1 426 012 A1 | 6/2004 |
| 2008/0029570 A1 | 2/2008 | Shelton et al. | EP | 1 459 695 | 9/2004 |
| 2008/0029571 A1 | 2/2008 | Shelton et al. | EP | 1477119 | 11/2004 |
| 2008/0029572 A1 | 2/2008 | Shelton et al. | EP | 1479345 | 11/2004 |
| 2008/0029573 A1 | 2/2008 | Shelton et al. | EP | 1 535 565 | 6/2005 |
| 2008/0029574 A1 | 2/2008 | Shelton et al. | EP | 1 566 150 | 8/2005 |
| 2008/0029575 A1 | 2/2008 | Shelton et al. | EP | 1 593 337 | 11/2005 |
| 2008/0029576 A1 | 2/2008 | Shelton et al. | EP | 1593337 | 11/2005 |
| 2008/0029577 A1 | 2/2008 | Shelton et al. | EP | 1 607 050 | 12/2005 |
| 2008/0035701 A1 | 2/2008 | Racenet et al. | EP | 1607050 | 12/2005 |
| 2008/0041916 A1 | 2/2008 | Milliman et al. | GB | 2109241 | 6/1983 |
| 2008/0041917 A1 | 2/2008 | Racenet et al. | GB | 2272159 | 5/1994 |
| 2008/0078802 A1 | 4/2008 | Hess et al. | GB | 2 284 242 | 5/1995 |
| 2008/0082124 A1 | 4/2008 | Hess et al. | JP | 2000033071 | 2/2000 |
| | | | JP | 2000171730 | 6/2000 |
| FOREIGN PATENT DOCUMENTS | | | JP | 2000325303 | 11/2000 |
| | | | JP | 2002143078 | 5/2002 |
| CA | 2512960 | 1/2006 | JP | 2005131163 | 5/2005 |
| CA | 2514274 | 1/2006 | JP | 2005131164 | 5/2005 |

| | | |
|---|---|---|
| JP | 2005131173 | 5/2005 |
| JP | 2005131211 | 5/2005 |
| JP | 2005131212 | 5/2005 |
| JP | 2005137423 | 6/2005 |
| JP | 2005152416 | 6/2005 |
| WO | 94/11057 | 5/1994 |
| WO | 00/48506 | 8/2000 |
| WO | 00/54653 | 9/2000 |
| WO | WO-00 72 762 A1 | 12/2000 |
| WO | WO-00/72765 A1 | 12/2000 |
| WO | WO-0162161 A1 | 8/2001 |
| WO | 02/43571 | 6/2002 |
| WO | WO-0243571 A2 | 6/2002 |
| WO | 03/000138 | 1/2003 |
| WO | 03/015604 | 2/2003 |
| WO | 03013363 | 2/2003 |
| WO | 03020106 | 3/2003 |
| WO | 03030743 | 4/2003 |
| WO | 03037193 | 5/2003 |
| WO | 03047436 | 6/2003 |
| WO | 03057048 | 7/2003 |
| WO | 03057058 | 7/2003 |
| WO | 03063694 | 8/2003 |
| WO | WO-03077769 A1 | 9/2003 |
| WO | 03079909 | 10/2003 |
| WO | 03082126 | 10/2003 |
| WO | 03088845 | 10/2003 |
| WO | 03090630 | 11/2003 |
| WO | 03094743 | 11/2003 |
| WO | 03094745 | 11/2003 |
| WO | 03094746 | 11/2003 |
| WO | 03094747 | 11/2003 |
| WO | 03101313 | 12/2003 |
| WO | 03105702 | 12/2003 |
| WO | 2004006980 | 1/2004 |
| WO | 2004/019769 | 3/2004 |
| WO | 2004/021868 | 3/2004 |
| WO | 2004/034875 | 4/2004 |
| WO | 2004032754 | 4/2004 |
| WO | 2004032760 | 4/2004 |
| WO | 2004032762 | 4/2004 |
| WO | 2004032763 | 4/2004 |
| WO | 2004/052426 | 6/2004 |
| WO | 2004047626 | 6/2004 |
| WO | 2004047653 | 6/2004 |
| WO | 2004049956 | 6/2004 |
| WO | 2004086987 | 10/2004 |
| WO | 2004/096015 | 11/2004 |
| WO | 2004096057 | 11/2004 |
| WO | 2004/103157 | 12/2004 |
| WO | 2004/105593 | 12/2004 |
| WO | 2004112618 | 12/2004 |
| WO | 2005027983 | 3/2005 |
| WO | 2005096954 | 10/2005 |
| WO | 2005115251 | 12/2005 |
| WO | 2006044490 | 4/2006 |
| WO | 2006044581 | 4/2006 |
| WO | 2006044810 | 4/2006 |
| WO | 2006083748 | 8/2006 |
| WO | 2006132992 | 12/2006 |
| WO | 2007016290 | 2/2007 |

OTHER PUBLICATIONS

Paul Breedveld, et al., "A New, Easily Miniaturized Sterrable Endoscope," IEEE Engineering in Medicine and Biology Magazine (Nov./Dec. 2005).

European Search Report, Application No. 07250393.1 dated Aug. 9, 2007 (8 pages) Disclosed Anonymously 'Motor-Driven Surgical Stapler Improvements' Research Disclosure Database No. 526041, Published: Feb. 2008.

Disclosed Anonymously 'Motor-Driven Surgical Stapler Improvements' Research Disclosure Database No. 526041, Published: Feb. 2008.

* cited by examiner

SURGICAL FASTENER AND CUTTER WITH SINGLE CABLE ACTUATOR

CROSS REFERENCE TO RELATED APPLICATIONS

The present application is a continuation-in-part of U.S. application Ser. No. 11/344,021 filed on Jan. 31, 2006 and entitled "Electro-Mechanical Surgical Cutting And Fastening Instrument Having A Rotary Firing And Closure System With Parallel Closure And Anvil Alignment Components," which is hereby expressly incorporated by reference in its entirety.

FIELD OF THE INVENTION

The present invention relates broadly to methods and devices for controlling movement and actuation of an end effector on a surgical device.

BACKGROUND OF THE INVENTION

Endoscopic surgical instruments are often preferred over traditional open surgical devices since the use of a natural orifice tends to reduce the post-operative recovery time and complications. Consequently, significant development has gone into a range of endoscopic surgical instruments that are suitable for precise placement of a working end of a tool at a desired surgical site through a natural orifice. These tools can be used to engage and/or treat tissue in a number of ways to achieve a diagnostic or therapeutic effect.

One tool commonly used in endoscopic surgery is a surgical stapler and cutter, which typically includes an end effector that simultaneously makes a longitudinal incision in tissue and applies lines of staples on opposing sides of the incision. The end effector includes a pair of cooperating jaw members that are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil. The instrument also includes a knife that cuts the stapled tissue.

Surgical staplers/cutters continue to increase in complexity and function with each generation due to the desire to introduce the devices endoscopically. However, endoscopic surgery requires that the shaft of the device be flexible while still allowing the end effector to be articulated and/or rotated to angularly orient the end effector relative to the tissue, and to be actuated to close the end effector and fire the staples. Integration of the controls for articulating, rotating, and/or actuating an end effector tend to be complicated by the use of a flexible shaft and by the size constraints of an endoscopic instrument. Generally, the control motions are all transferred through the shaft as longitudinal translations, which can interfere with the flexibility of the shaft.

There is also a desire to lower the force necessary to actuate the end effector to a level that all or a great majority of surgeons can handle. One known solution to lower the force-to-fire is to use electrical motors. However, surgeons typically prefer to experience feedback from the end-effector to assure proper operation of the end effector. The user-feedback effects are not suitably realizable in present motor-driven devices.

Accordingly, there remains a need for improved methods and devices for controlling movement and actuation of an end effector on an endoscopic surgical device.

SUMMARY OF THE INVENTION

The present invention generally provides methods and devices for controlling movement, i.e., rotation, and actuation, i.e., closing and firing, of an end effector on an endoscopic surgical device. In one exemplary embodiment, an endoscopic stapling device is provided and includes an elongate shaft having proximal and distal ends, an end effector coupled to a distal end of the elongate shaft for engaging tissue and delivering at least one fastener to the engaged tissue, a handle coupled to a proximal end of the elongate shaft, and an actuator operatively associated with the end effector and the handle. The actuator has a first position in which rotation of the actuator is effective to rotate the end effector, and a second position in which rotation of the actuator is effective to fire at least one fastener from the end effector. The actuator can also be adapted to translate along a longitudinal axis of the elongate shaft between the first and second positions. Translation of the actuator from the first position to the second position can be effective to close the end effector for engaging tissue.

The end effector can have a variety of configurations, but in one embodiment, the end effector can include opposed jaws for engaging tissue therebetween. The actuator can include a clutch on the distal end thereof, and, when the actuator is translated from the first position to the second position, the clutch can be adapted to abut against a cam surface formed on at least one of the jaws to close the jaws. The end effector can also include a cartridge removably disposed therein and containing a plurality of staples for stapling tissue and a blade for cutting stapled tissue.

The actuator can also have a variety of configurations, but in one embodiment it can be a rotatable and translatable drive shaft operatively associated with the handle and the end effector. The drive shaft can include a clutch on a distal end thereof. When the actuator is in the first position, the clutch can be adapted to engage a housing of the end effector such that rotation of the actuator and the clutch is effective to rotate the end effector. When the actuator is in the second position, the clutch can be adapted to engage and rotate a gear assembly that advances a driver disposed within the end effector to fire at least one fastener from the end effector. In other embodiments, at least a portion of the drive shaft can be formed from an electroactive polymer material, and wherein the handle is effective to deliver energy to the drive shaft to cause the electroactive polymer material to axially contract and radially expand and thereby translate the drive shaft.

The handle of the device can also have a variety of configurations, and in one embodiment the handle can include a translating member that is adapted to translate the actuator between the first and second positions, and a rotatable member that is adapted to rotate the actuator relative to the elongate shaft. The device can also include other features, such as an optical image gathering unit disposed on a distal end of the elongate shaft and configured to acquire images during endoscopic procedures. The optical image gathering unit can couple to an external image display screen, or an image display screen can be disposed on a proximal portion of the device for communicating with the optical image gathering unit to display the acquired images.

In another embodiment, an endoscopic stapling device is provided having an elongate shaft with an end effector coupled to a distal end thereof, a handle movably coupled to a proximal end thereof, and a drive shaft operatively associated with the handle and the end effector and adapted to rotate the end effector relative to the elongate shaft, to close the end effector to engage tissue, and to fire at least one fastener from the end effector. The drive shaft can be movable between a first position, in which rotation of the drive shaft causes corresponding rotation of the end effector relative to the elongate shaft without closing and firing the end effector, and a second position, in which rotation of the drive shaft causes closing and firing of the end effector without rotating the end effector relative to the elongate shaft. The drive shaft can also be adapted to translate relative to a longitudinal axis of the elongate shaft to move between the first and second positions. Translation of the drive shaft from the first position to the second position can be adapted to close opposed jaws of the end effector. For example, a distal end of the drive shaft can engage a portion of the end effector to rotate the end effector when the drive shaft is in the first position, and a distal end of the drive shaft can engage a gear assembly to rotate the gear assembly when the drive shaft is in the second position. Rotation of the gear assembly can be effective to advance a driver disposed within the end effector to fire at least one fastener from the end effector.

Methods for fastening tissue are also provided, and in one exemplary embodiment the method includes inserting an elongate shaft into a body lumen to position an end effector coupled to a distal end of the elongate shaft adjacent to tissue to be fastened. A proximal end of the elongate shaft can include a handle assembly movably coupled thereto. The method can further include rotating a rotatable member in a first position on the handle assembly to rotate the end effector about a longitudinal axis of the elongate shaft, and rotating the rotatable member in a second position on the handle assembly to fire at least one fastener disposed within the end effector without rotating the end effector. The method can also include moving a translating member on the handle assembly to close opposed jaws of the end effector around tissue to be fastened. While the method can be used in various procedures, in certain exemplary embodiments the elongate shaft is flexible and is inserted translumenally.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides method and devices for controlling movement, i.e., rotation, and actuation, i.e., closing and/or firing, of an end effector on a surgical stapling device. In general, the surgical stapling device can include an elongate shaft having a distal end with an end effector extending therefrom for engaging tissue and delivering one or more fasteners to the engaged tissue, and a proximal end with a handle for controlling rotation of the end effector whereby the end effector swivels about the longitudinal axis of the elongate shaft, and actuation of the end effector whereby the end effector is closed and fired to deliver one or more fasteners and optionally cut tissue being fastened. In an exemplary embodiment, the device includes a single actuation mechanism that is configured to effect both rotation and actuation of the end effector. The actuation mechanism can be operatively associated with the handle and the end effector and it can have a first position in which the actuation mechanism is effective to rotate the end effector without actuating the end effector, and a second position in which the actuation mechanism it is effective to fire at least one fastener from the end effector without rotating the end effector. The actuation mechanism can also be configured such that movement from the first position to the second position is effective to close the end effector to engage tissue. Various other features are also provided to facilitate use of the device. A person skilled in the art will appreciate that the particular configuration of the end effector can vary and that the various control techniques described herein can be used on a variety of surgical instruments.

Figure 1A:
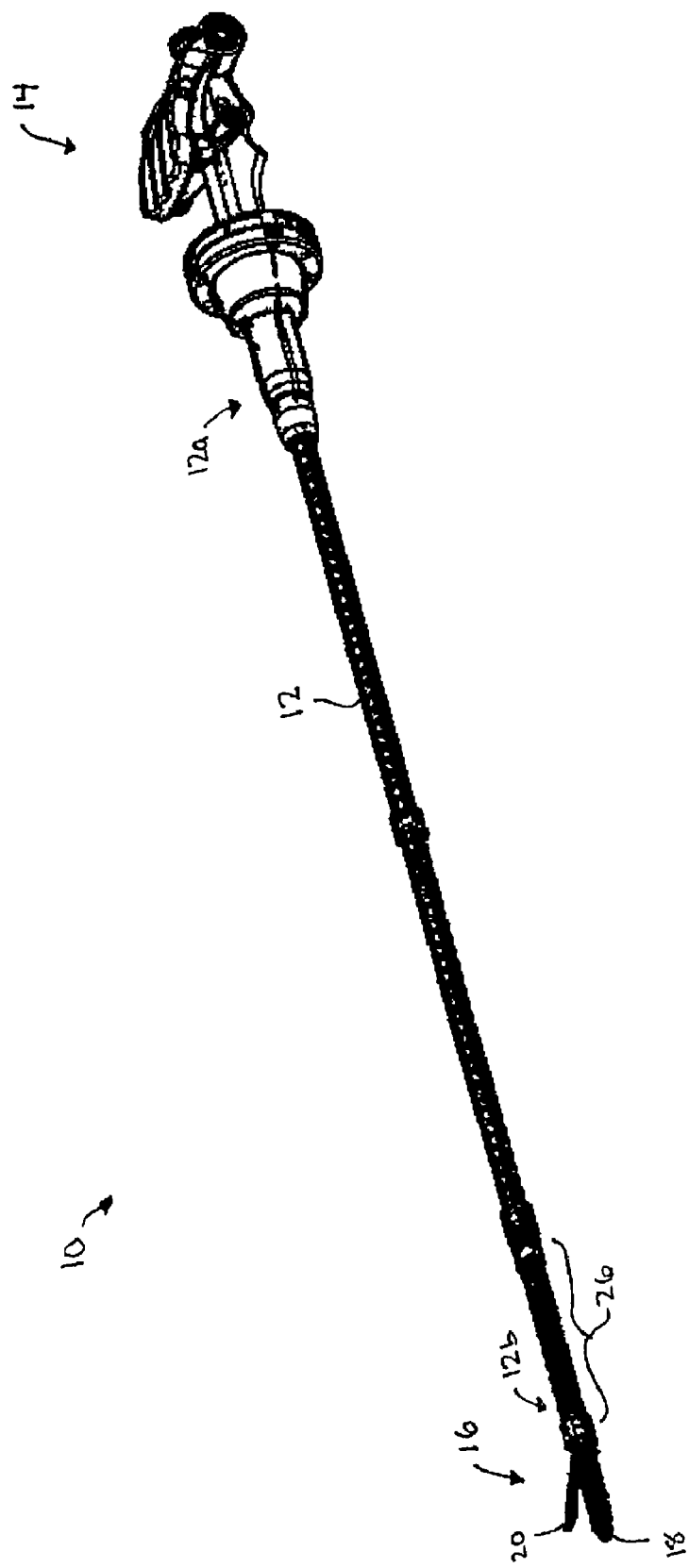
FIG. 1A is a perspective view of one exemplary embodiment of a surgical stapling device in accordance with the present invention.
Figure 1B:
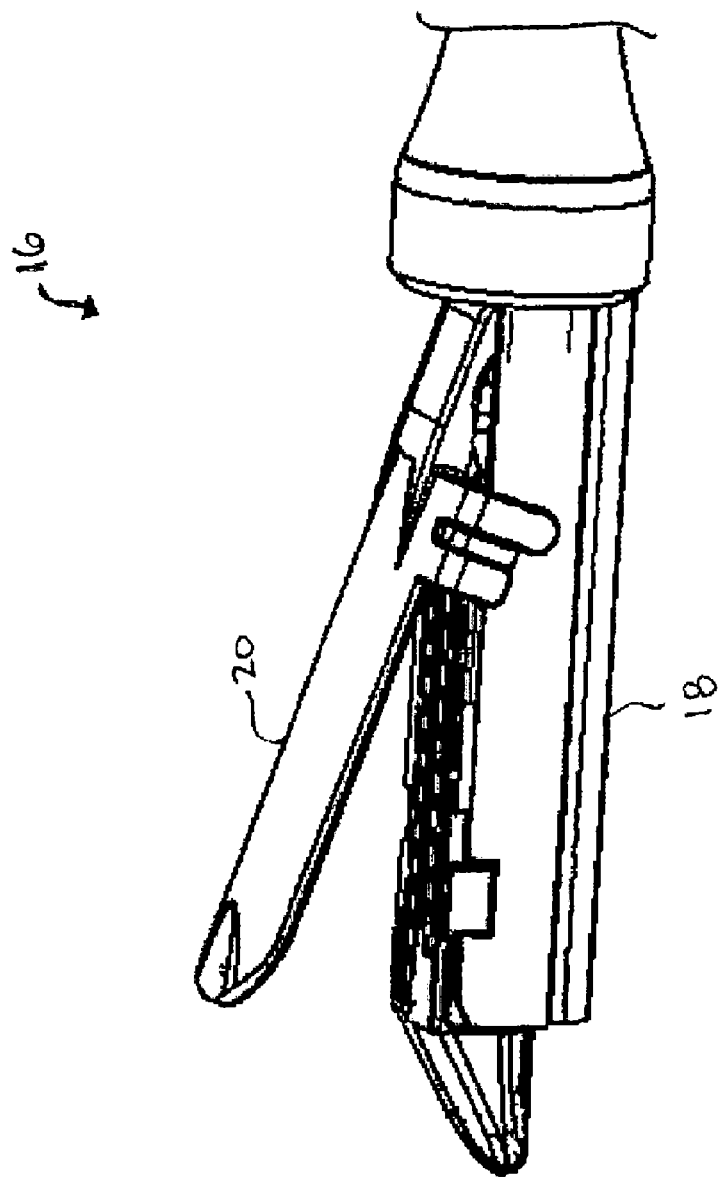
FIG. 1B is a perspective view of an end effector of the surgical stapling device of FIG. 1A.

FIG. 1A illustrates one exemplary embodiment of an endoscopic surgical device that is in the form of a linear stapling and cutting device 10 for applying multiple linear rows of staples to tissue and for cutting the stapled tissue. As shown, the device 10 generally includes an elongate shaft 12 having a proximal end 12a with a handle 14 coupled thereto, and a distal, working end 12a having an end effector 16 coupled thereto or formed thereon. The elongate shaft 12 can have a variety of configurations. For example, it can be solid or hollow, and it can be formed from a single component or multiple segments. As shown in FIG. 1A, the elongate shaft 12 is hollow and is formed from multiple connecting segments to allow the elongate shaft 12 to flex. The flexibility of the shaft 12, as well as a relatively small diameter, allows the shaft 12 to be used in endoscopic procedures, whereby the device is introduced translumenally through a natural orifice. The end effector 16 can also have a variety of configurations, but in the illustrated embodiment, as shown in more detail in FIG. 1B, the end effector 16 includes opposed first and second jaws 18, 20 that are that are pivotally coupled to one another and that are adapted to receive tissue therebetween. The first jaw 18 is adapted to contain a staple cartridge having multiple staples disposed therein and configured to be driven into tissue, and the second jaw 20 forms an anvil for deforming the staples. The end effector 16 can be coupled to the distal end of the elongate shaft using various techniques, but in an exemplary embodiment the end effector 16 is rotatably coupled to the elongate shaft such that the end effector 16 can rotate about an axis of the elongate shaft. The end effector 16 can also be pivotally coupled to the distal end of the elongate shaft, or it can include a flexible neck 26 formed thereon for allowing angular movement of the end effector relative to the elongate shaft.

While not an essential feature of the present invention, FIG. 1A also illustrates a handle 14 that is operatively associated with the end effector 16 such that pivotal movement of the handle 14 is mimicked by the end effector 16, thereby allowing the handle 14 to be used to articulate the end effector 16 in multiple planes. The particular mechanism for achieving mimicking motion is described in more detail in the following U.S. patent applications filed on even date herewith: "Methods and Devices for Controlling Articulation, Ser No. 11/277,323," by Mark S. Ortiz, Frederick E. Shelton IV, and James Spivey, "Articulating Endoscopic Accessory Channel, Ser. No. 11/277,324," by James Spivey, Mark S. Ortiz, and Frederick E. Shelton IV, and "Surgical Fastener and Cutter with Mimicking End Effector, Ser. No. 11/277, 328," by Mark S. Ortiz and Frederick E. Shelton IV, each of which is hereby incorporated by reference in its entirety.

Figure 2:
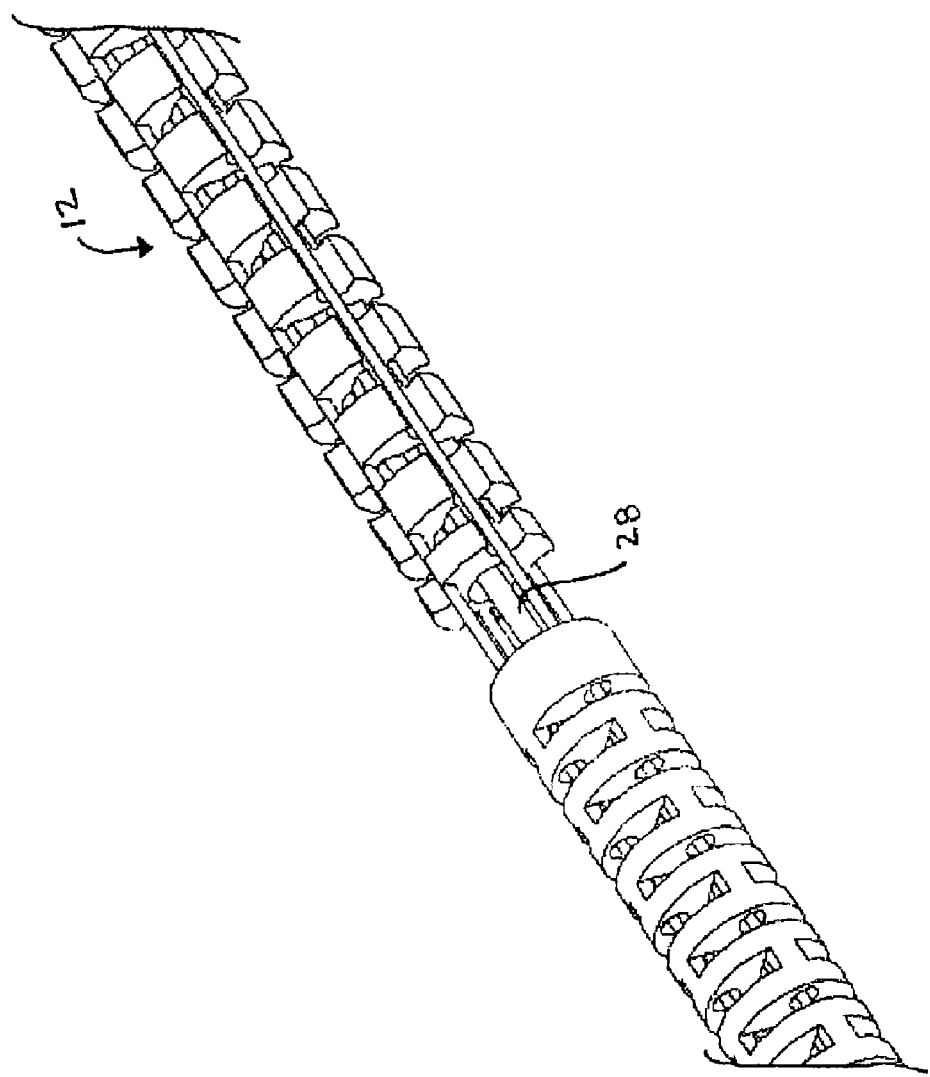
FIG. 2 is a perspective, partially cut-away view of a portion of an elongate shaft of the surgical stapling device of FIG. 1A, showing a drive shaft extending through the elongate shaft.

The device 10 can also include an actuation mechanism for controlling movement and actuation of the end effector 16. Movement can include rotation of the end effector 16 about the longitudinal axis A of the elongate shaft 12, and actuation of the end effector, whereby the jaws 18, 20 are closed to engage tissue and the staples are fired from the end effector into the engaged tissue. Actuation can also include cutting the stapled tissue. In an exemplary embodiment, a single actuation mechanism is operatively associated with the handle and the end effector such that it can effect rotation and actuation of the end effector. While the actuation mechanism can have a variety of configurations, in the illustrated embodiment the actuation mechanism is in the form of a drive shaft 28, which is shown in FIG. 2 extending through a portion of the elongate shaft 12. The drive shaft 28 can be in the form of an elongate cable, multiple wound or braided cables, or a rod or shaft, and it is preferably flexible to allow flexion as the flexible shaft 12 of the device 10 is inserted translumenally through a tortuous pathway. The drive shaft 28 includes proximal and distal ends that are coupled to various portions of the handle 14 and the end effector 16, respectively, as will be discussed in more detail below. In use, the drive shaft 28 is configured to rotate and translate (slide) relative to the elongate shaft 12 to effective rotation and actuation of the end effector 16.

Figure 3:
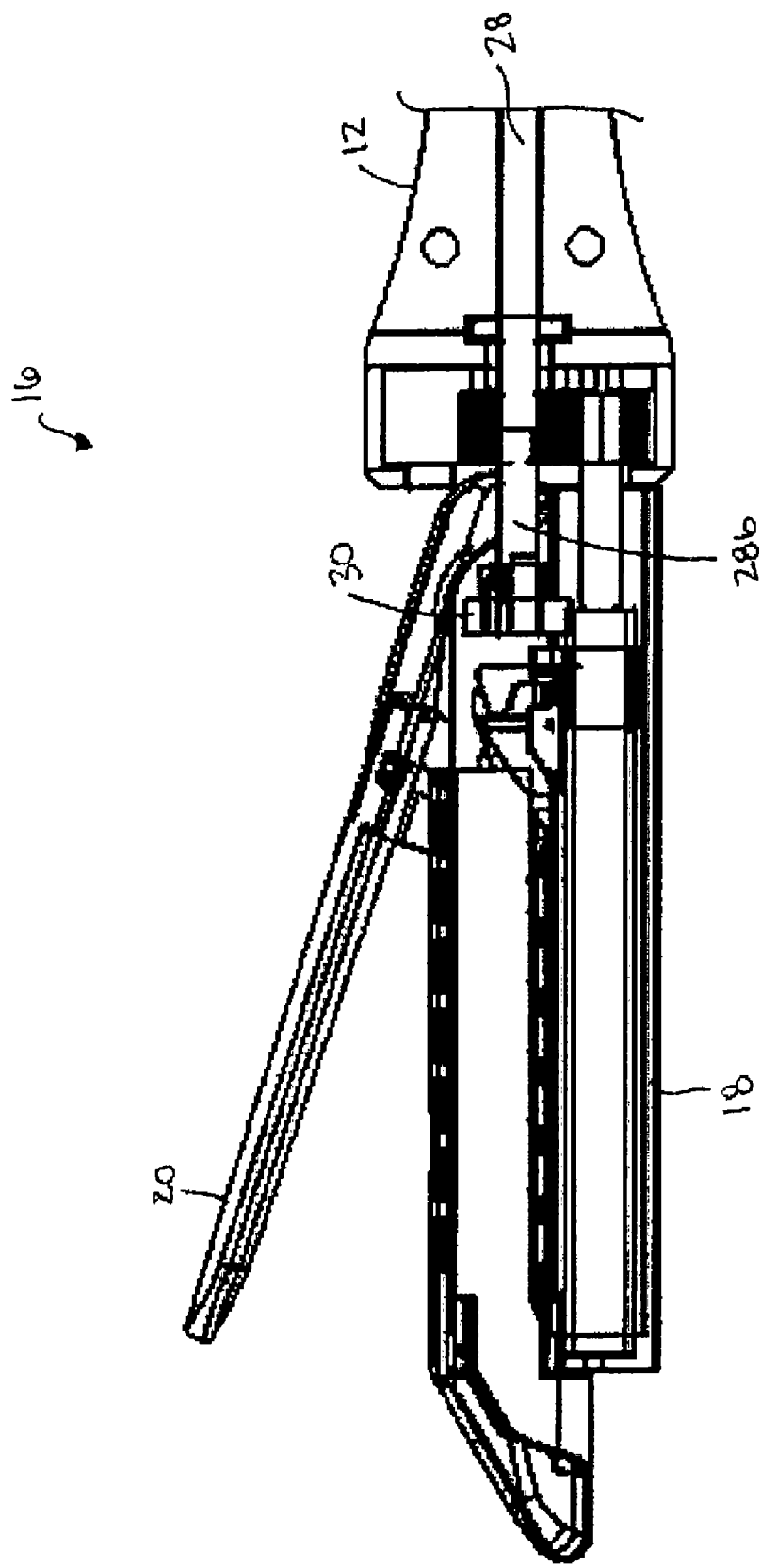
FIG. 3 is a side cross-sectional view of the end effector of the surgical stapling device of FIG. 1A.
Figure 4:
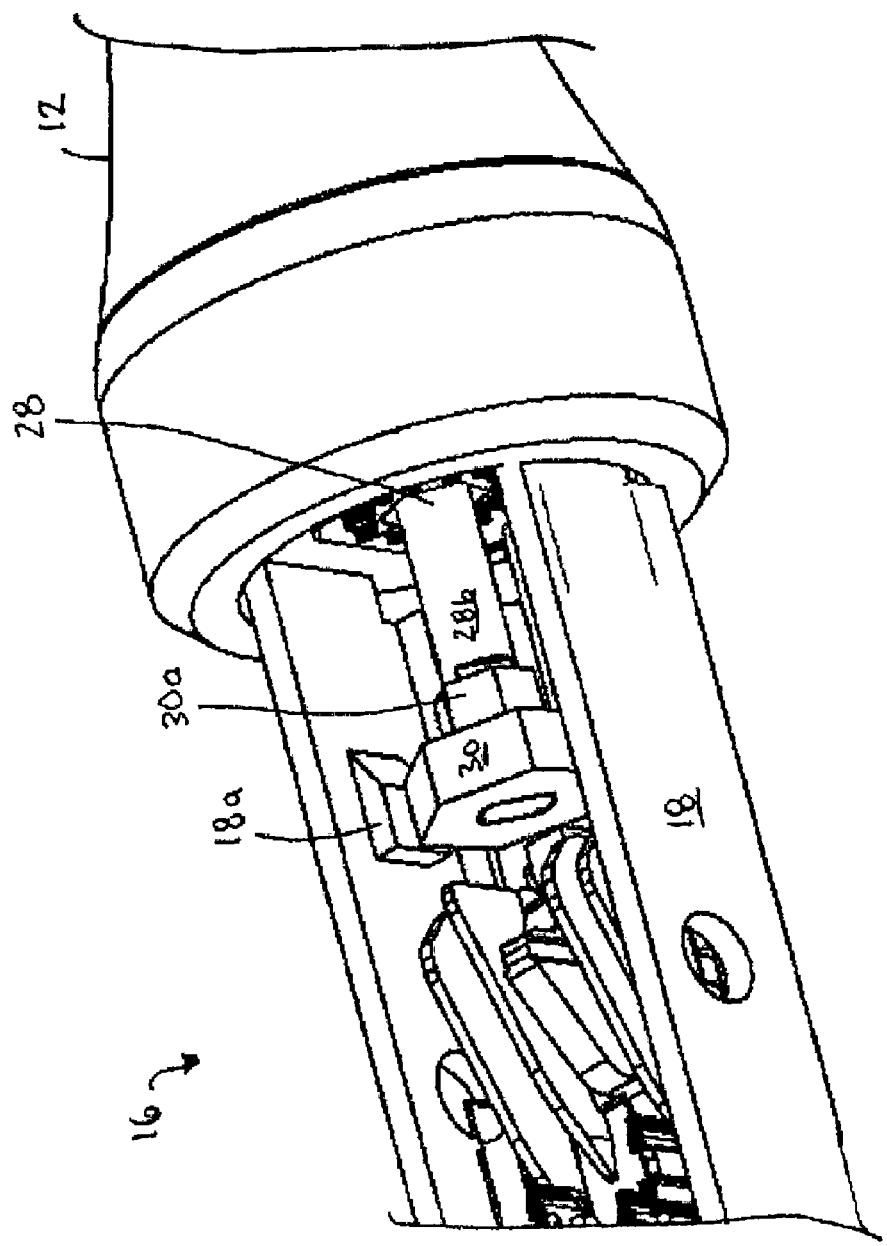
FIG. 4 is a top view of a portion of the end effector of the surgical stapling device of FIG. 1A, showing a clutch engaging the end effector to effect rotation thereof.

The distal end 28b of the drive shaft 28 and the end effector 16 are shown in more detail in FIG. 3, and as shown the distal end 28b of the drive shaft 28 extends distally from the elongate shaft 12 and extends into a proximal end of the end effector 16. The distal end 28b of the drive shaft 28 is preferably configured to rotate the end effector 16 when the drive shaft 28 is in a first position, and to fire the end effector 16 when the drive shaft 28 is in a second position. Movement of the drive shaft 28 from the first position to the second position can also be effective to close the jaws 18, 20 of the end effector 16. While various techniques can be used to allow the drive shaft 28 to effect rotation, closing, and firing of the end effector 16, in the illustrated embodiment the distal end 28b of the drive shaft 28 includes a clutch 30 formed thereon or fixedly mated thereto. The clutch 30 can have various shapes and sizes, but it is preferably asymmetrical to allow the clutch 30 to engage various mechanism within the end effector 16, as will be discussed below. In the illustrated embodiment, the clutch 30 has a hexagonal shape. When the clutch 30 is in a first position, e.g., a distal position shown in FIG. 3, it can be in engaged with the end effector 16 such that rotation of the drive shaft 28 and the clutch 30 is effective to rotate the end effector 16. In particular, as shown in FIG. 4, the opposed inner walls of first jaw 18 can include opposed protrusions (only one protrusion 18a is shown in FIG. 4) formed thereon that are configured to engage the clutch 30 therebetween. Thus, when the clutch 30 is positioned between the protrusions, rotation of the clutch 30 is effective to rotate the end effector 16 about its longitudinal axis and relative to the elongate shaft 12.

Figure 5A:
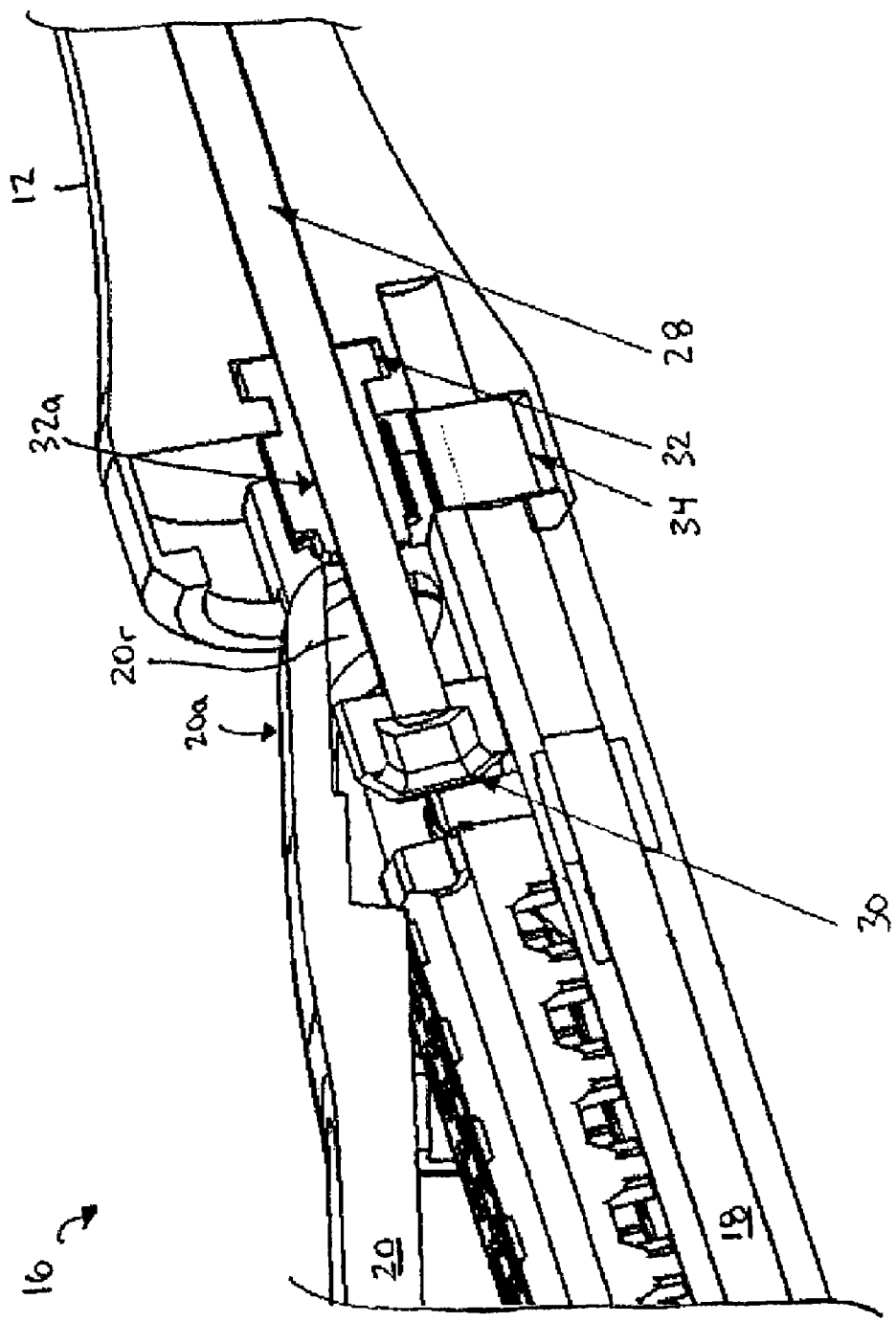
FIG. 5A is an enlarged side cross-sectional view of a portion of the end effector of FIG. 1A.
Figure 5B:
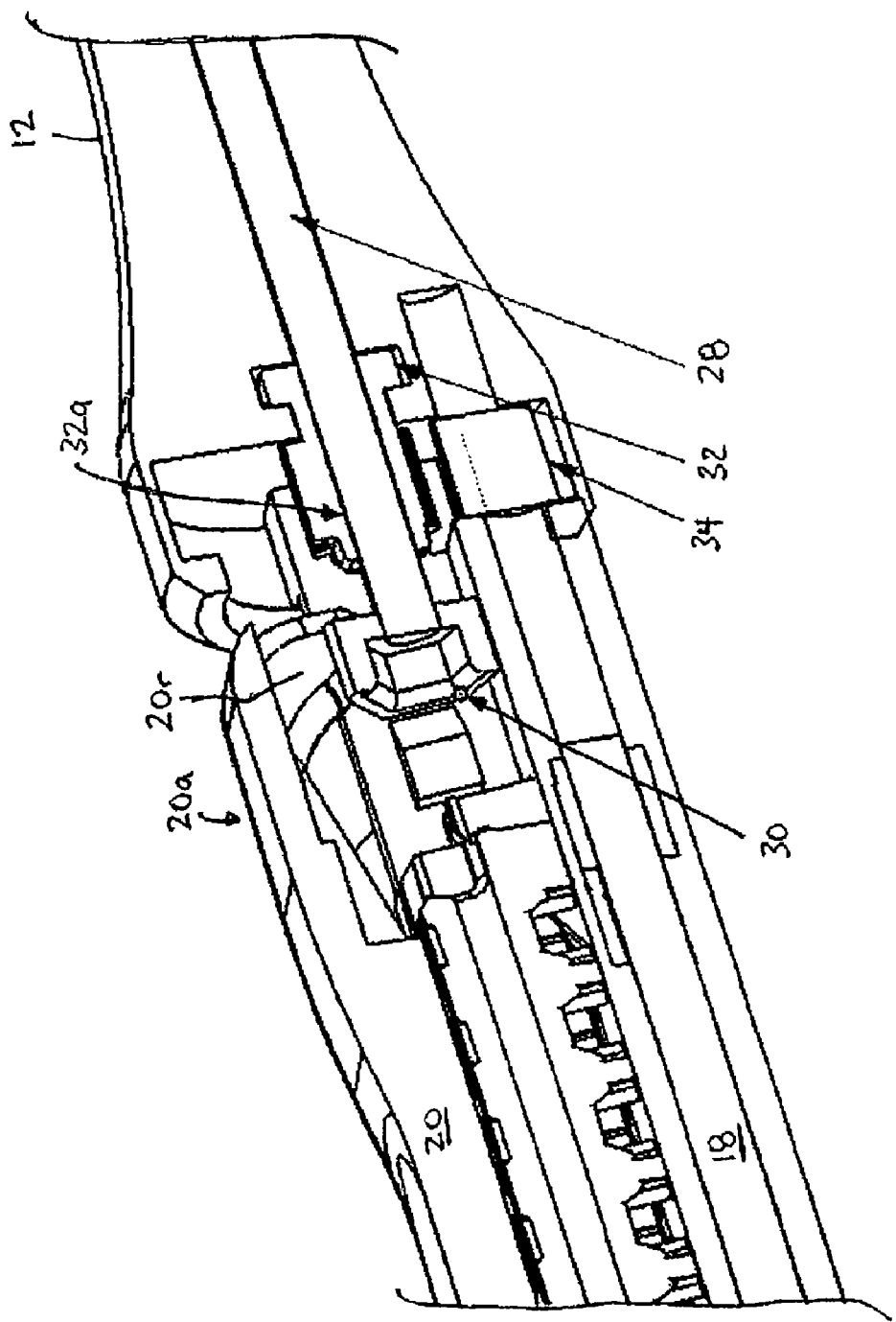
FIG. 5B is a side cross-sectional view of the end effector shown in FIG. 5A, showing the jaws moved to a closed position.

Once the end effector 16 is rotated to a desired position, the drive shaft 28 and clutch 30 can be moved axially relative to the elongate shaft 12 to remove the clutch 30 from between the protrusions in the first jaw 18. In an exemplary embodiment, the drive shaft 28 and clutch 30 are translated along the elongate shaft 12 in a proximal direction to position the drive shaft 28, and thus the clutch 30, in the second position. As the drive shaft 28 and clutch 30 are moved proximally, the drive shaft 28 and clutch 30 can be effective to close the jaws 18, 20 of the end effector 16. In particular, as shown in FIG. 5, the second jaw, i.e., the anvil 20, can include a proximal end 20a having a ramped surface 20r formed thereon and extending into a path of movement of the clutch 30. The ramped surface 20r on the anvil 20 is located proximal to a pivot point at which the anvil 20 is attached to the first jaw 18. As the clutch 30 moves proximally with the drive shaft 28, the clutch 30 can abut against the ramped surface 20r, pushing the surface upward away from the first jaw 18. As a result, the anvil 20 will pivot to a closed position, as shown in FIG. 5B, to engage tissue positioned between the jaws 18, 20. When the drive shaft 28 and clutch 30 are in the second proximal position, the second jaw or anvil 20 will remain closed as the clutch 30 will prevent the proximal end 20a of the second jaw or anvil 20 from returning to its initial position.

Figure 6:
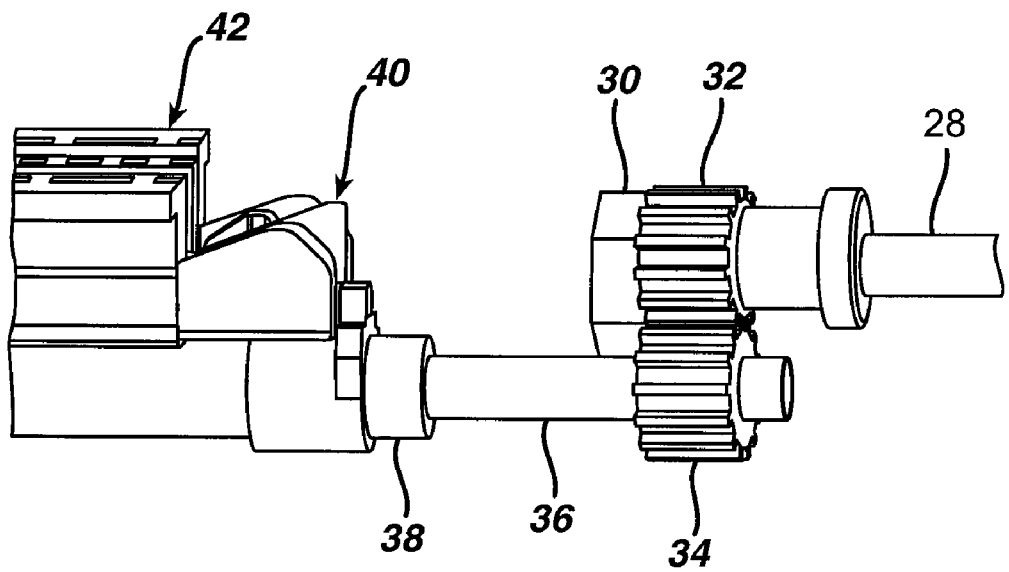
FIG. 6 is a side view of a portion of the end effector of FIG. 1A, showing a gear and driver assembly.
Figure 7:
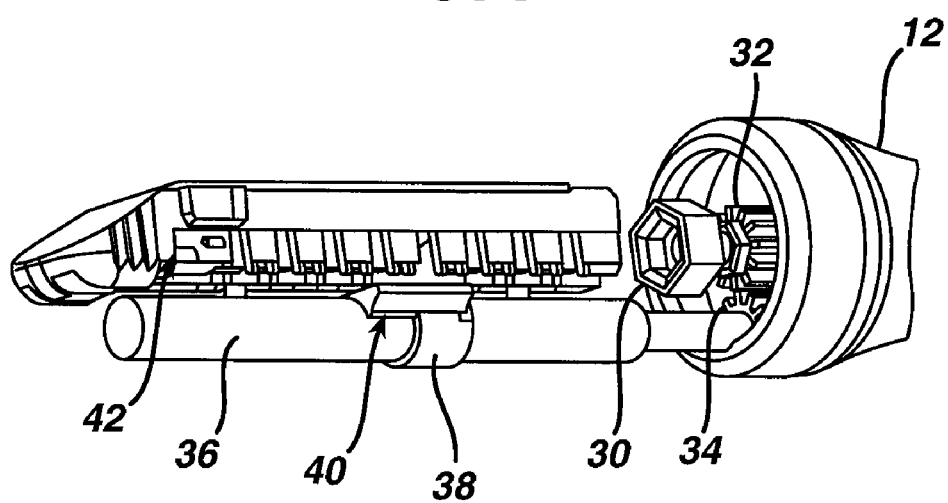
FIG. 7 is a perspective view of a portion of the end effector of FIG. 1A, showing a lead screw being driven through the end effector to fire staples from the cartridge.

Once the drive shaft 28 and clutch 30 are in the second position, rotation of the drive shaft 28 and clutch 30 can be effective to fire at least one fastener from the jaws 18, 20. In particular, the clutch 30 can be configured to engage a gear assembly that is effective to advance a driver through the end effector 16. The gear assembly is shown in FIG. 6 and includes first (upper) and second (lower) drive gears 32, 34 that are in the form of cylindrical members having teeth formed therearound. The first drive gear 32 includes a socket 32a (shown in FIGS. 5A and 5B) formed therein that has a shape that complements a shape of a portion of the clutch 30 such that the socket 32a can receive and engage the clutch 30 on the drive shaft 28. In particular, the clutch 30 can include a second hexagonal member 30a (FIG. 4) formed thereon and configured to be received in the socket 32a. The second drive gear 34 is positioned adjacent to and in engagement with the first drive gear 32. As a result, when the drive shaft 28 and clutch 30 are rotated, the first drive gear 32 will rotate to rotate the second drive gear 34. The second drive gear 34, in turn, includes a shaft or lead screw 36 extending distally therefrom and fixedly coupled thereto. The lead screw 36 has threads (not shown) formed on an external surface thereof, and a lead nut 38 is threadably disposed around the lead screw 36. As the second drive gear 34 and lead screw 36 are rotated, the lead screw 36 remains in a fixed axial position, i.e., it does not translate longitudinally, thereby causing the lead nut 38 to move distally through the end effector 16, as shown in FIG. 7. The lead nut 38, in turn, is coupled to or abuts against a proximal end of a drive sled 40 that is effective to drive one or more fasteners from a cartridge 42 disposed within the first jaw 18. Thus, as the drive shaft 28 and clutch 30 are rotated, the first drive gear 32 rotates to rotate the second drive gear 34 and the lead screw 36 attached thereto. As the lead screw 36 rotates, the lead nut 38 is moved distally within the end effector 16, thereby advancing the drive sled 40 distally within the end effector 16. The drive sled 40 will force one or more fasteners through one or more fastener receiving slots formed in the cartridge 42. The fasteners will extend through tissue engaged between the jaws 18, 20, and will deform against the anvil 20 to fasten the tissue. The drive sled 40 can also include a blade formed thereon and configured to cut tissue being fastened.

Figure 8A:
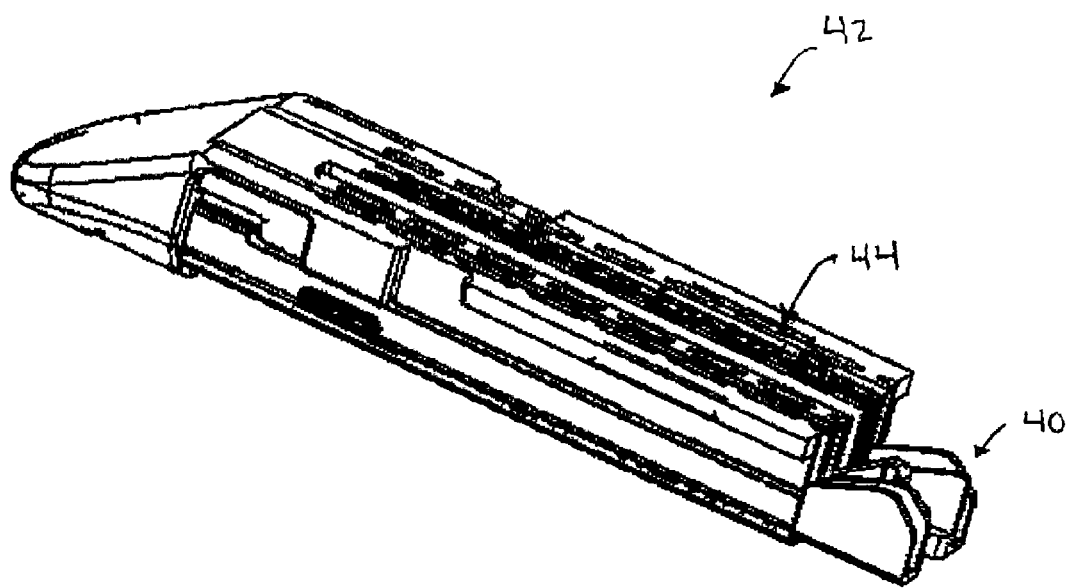
FIG. 8A is a perspective view of a cartridge of the end effector of FIG. 1A.
Figure 8B:
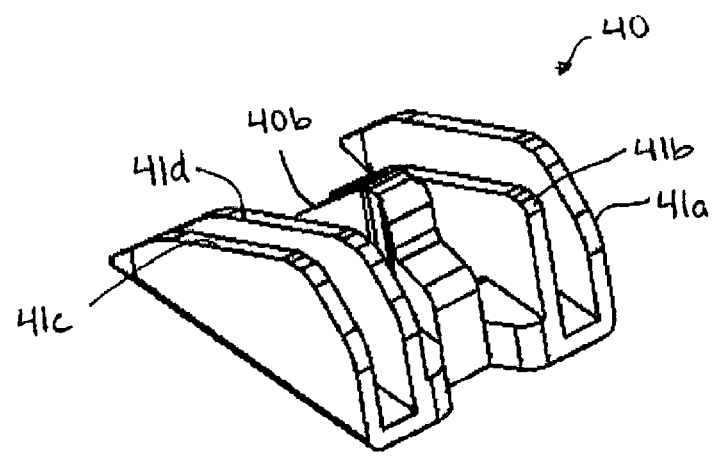
FIG. 8B is a perspective view of a drive sled of the cartridge of FIG. 8A.

While the particular configuration of the drive sled 40 and the cartridge 42 can vary depending on the particular configuration of the end effector 16, in an exemplary embodiment, as shown in FIG. 8A, the cartridge 42 is configured to apply multiple linear rows of staples, and to form a cut extending between the rows of staples to separate the stapled tissue. In particular, the cartridge 42 is in the form of a generally elongate housing that can be removably disposed within a channel formed in the first jaw 18. The housing includes several, e.g., six, linear rows of staple-receiving slots 44 formed therein, and each slot contains a staple therein. Several driver members (not shown) are positioned underneath the staples for supporting the staples and advancing the staples through the staple-receiving slots 44. The drive sled 42 is shown in more detail in FIG. 8B and it includes several, e.g., four, upright members 41a, 41b, 41c, 41d formed thereon and having a wedge-shaped configuration. As the sled 40 is advanced distally through the end cartridge 40, the upright members 41a-d will abut against the driver members, moving them upward toward the anvil 20, thereby driving the staples toward the anvil 20. The drive sled 40 also includes a central member that extends through the middle of the cartridge, and that has a blade 40b formed thereon for cutting the stapled tissue.

In use, the cartridge 42, with the drive sled 40 coupled thereto, can be disposed within the end effector 16 for a single use application. Once the staples are fired from the cartridge 42, a new cartridge having a new drive sled 40 can be placed in the jaw 18. Such a configuration is particularly advantageous as the blade 40b can be replaced with each use, rather than most stapling devices in which the drive sled and blade are disposed within the jaw of the end effector, rather than being removable with the cartridge. A person skilled in the art will appreciate that virtually any cartridge known in the art can be used with the various devices disclosed herein, and that the illustrated cartridge 42 is merely one exemplary embodiment of a cartridge.

Figure 9A:
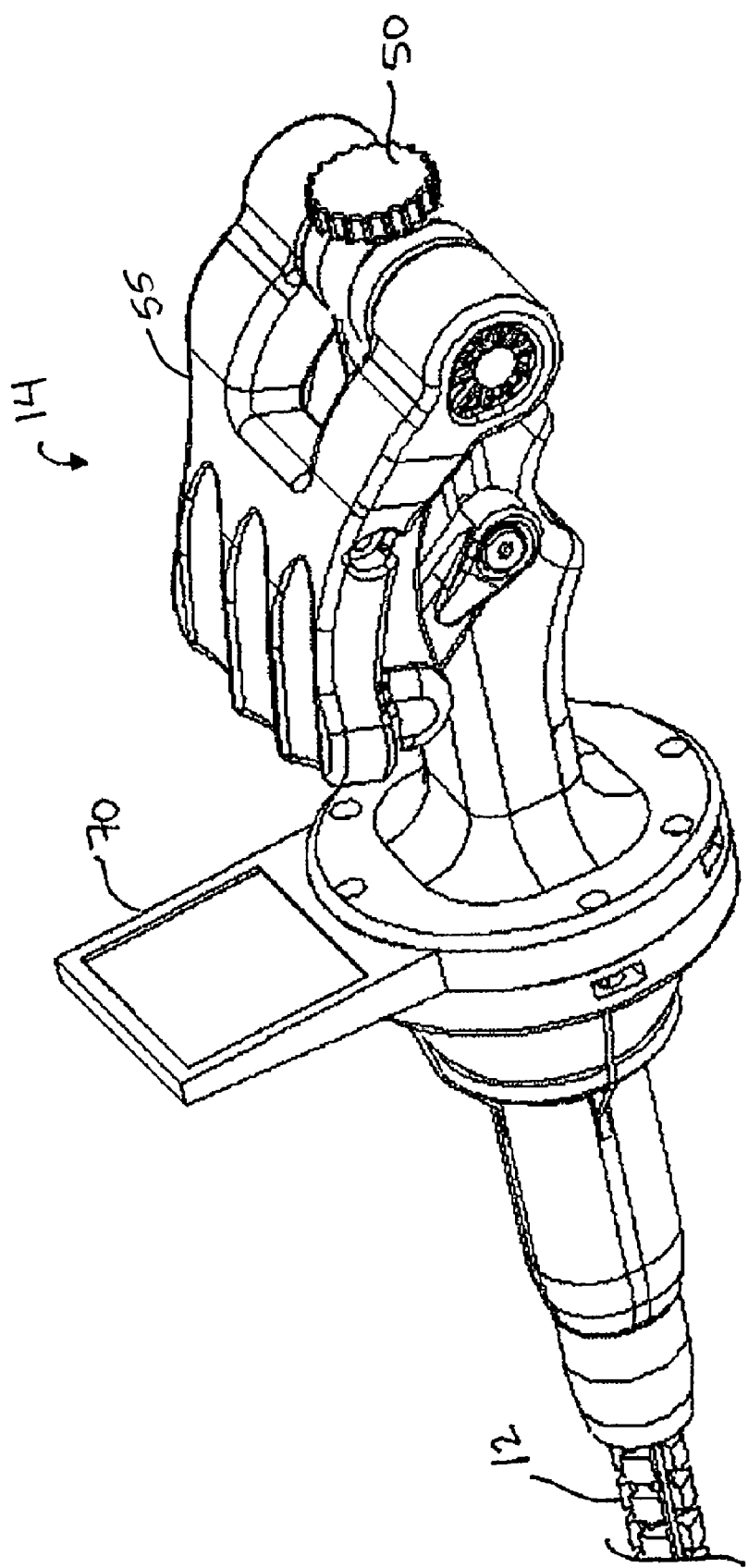
FIG. 9A is a perspective view of a handle of the device of FIG. 1A.
Figure 9B:
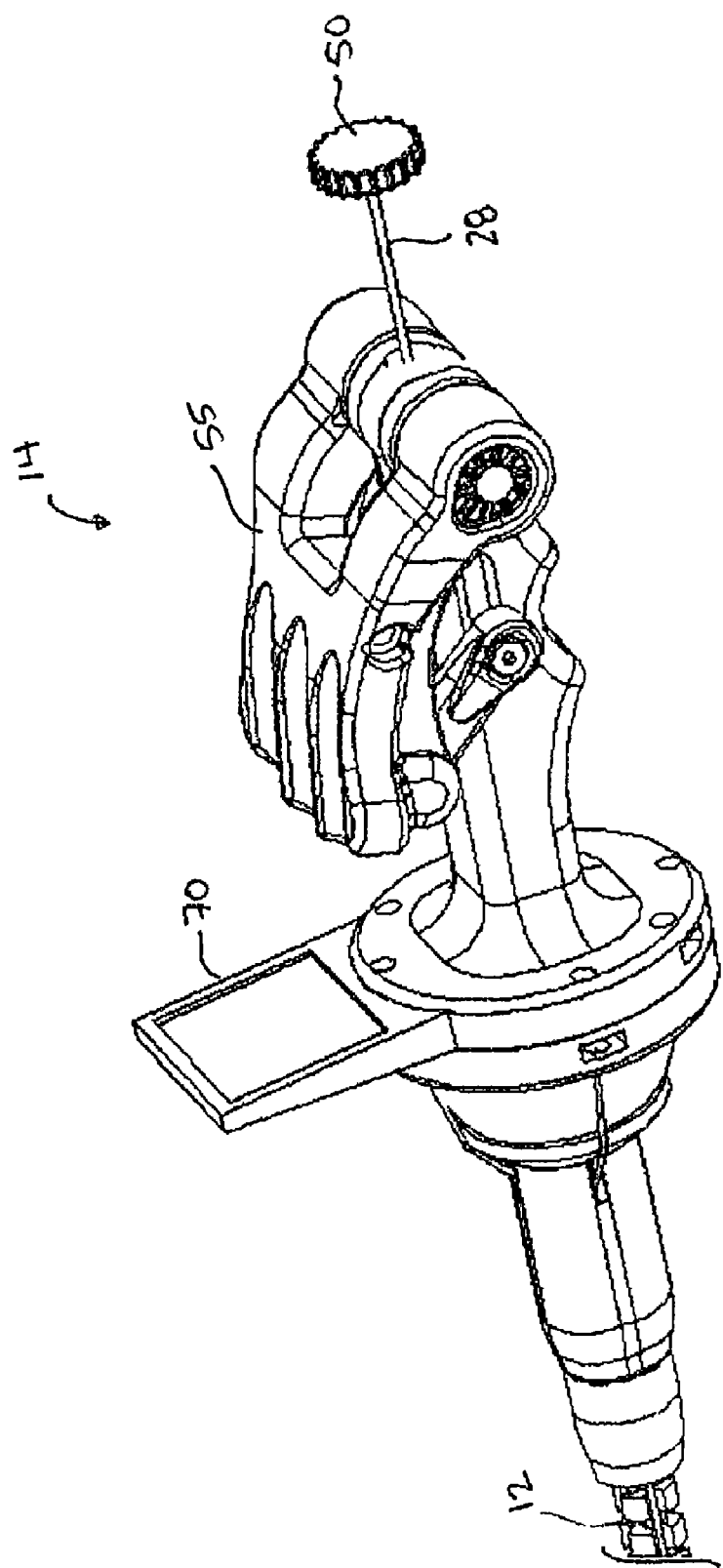
FIG. 9B is a perspective view of the handle of FIG. 9A, showing a knob in a second position.

As indicated above, the proximal end of the drive shaft 28 is coupled to various portions of the handle 14 that are effective to rotate the drive shaft 28 in the first position to thereby rotate the end effector 16, to translate the drive shaft 28 axially into a second position to thereby close the jaws 18, 20, and to rotate the drive shaft 28 in the second position to fire the staples from the cartridge 42 in the end effector 16. While various techniques known in the art can be used to effect rotation and translation of the drive shaft 28, in one exemplary embodiment the handle 14 can include a rotatable and translatable knob 50 for rotating and translating the drive shaft 28 relative to the elongate shaft 12 of the device 10. The knob 50 of the handle 14 is shown in more detail in FIG. 9A and 9B, and as shown the knob 50 is merely a cylindrical member disposed on the proximal-most end of the handle 14 and coupled to the proximal end of the drive shaft 28. FIG. 9A illustrates the knob 50 in a first position, in which rotation of the knob 50 will rotate the drive shaft 28 to thereby rotating the end effector 16. FIG. 9B illustrates the knob 50 moved proximally to a second position, i.e., retracted relative to the elongate shaft 12, to thereby close the jaws 18, 20. Movement of the knob 50 can be achieved by simply pulling on the knob 50, or alternatively the device 10 can include a separate translating member 55 formed on the handle 14 and coupled to the drive shaft 28 for moving the drive shaft 28, and consequently the knob 50) between the first and second positions. In an exemplary embodiment, as shown, the translatable member 55 is shaped to fit within a palm of a user's hand. A toggle link or over-center link extends between the translatable member 55 and the handle 14 for controlling movement of the translatable member 55 relative to the handle. In use, the translatable member 55 can be squeezed to close the translatable member 55, thereby applying a proximally directed force to the drive shaft 28 to move the drive shaft 28 to the second position, shown in FIG. 9B. Rotation of the knob 50 in the second position will be effective to fire the staples from the cartridge 42, as previously explained, thereby stapling the tissue engaged between the jaws. The tissue can also be cut simultaneous with or subsequent to firing the staples. A person skilled in the art will appreciate that the particular location and configuration of the knob or other member used to effect rotation and translation of the drive shaft 28 can vary.

While FIGS. 9A-9B illustrate a rotatable and translatable knob, in other embodiments, the drive shaft 28 used to effect rotation and actuation of the end effector 16 can optionally be formed from an electroactive polymer material. Electroactive polymers (EAPs), also referred to as artificial muscles, are materials that exhibit piezoelectric, pyroelectric, or electrostrictive properties in response to electrical or mechanical fields. In particular, EAPs are a set of conductive doped polymers that change shape when an electrical voltage is applied. The conductive polymer can be paired to some form of ionic fluid or gel and electrodes, and the flow of ions from the fluid/gel into or out of the conductive polymer can induce a shape change of the polymer. Typically, a voltage potential in the range of about 1V to 4 kV can be applied depending on the particular polymer and ionic fluid or gel used. It is important to note that EAPs do not change volume when energized, rather they merely expand in one direction and contract in a transverse direction. Thus, the drive shaft 28 previously disclosed herein can be replaced by an EAP actuator, and the handle 14 can be configured to activate an external or internal energy source to selectively deliver energy to the EAP cable to cause the EAP cable to axially contract and move the clutch 30 from the first position to the second position. The EAP cable can then be rotated, e.g., using a rotatable knob, to fire one or more staples from the end effector 16. When energy delivery is terminated, the EAP cable will axially expand to return the clutch 30 to the first position.

Figure 10:
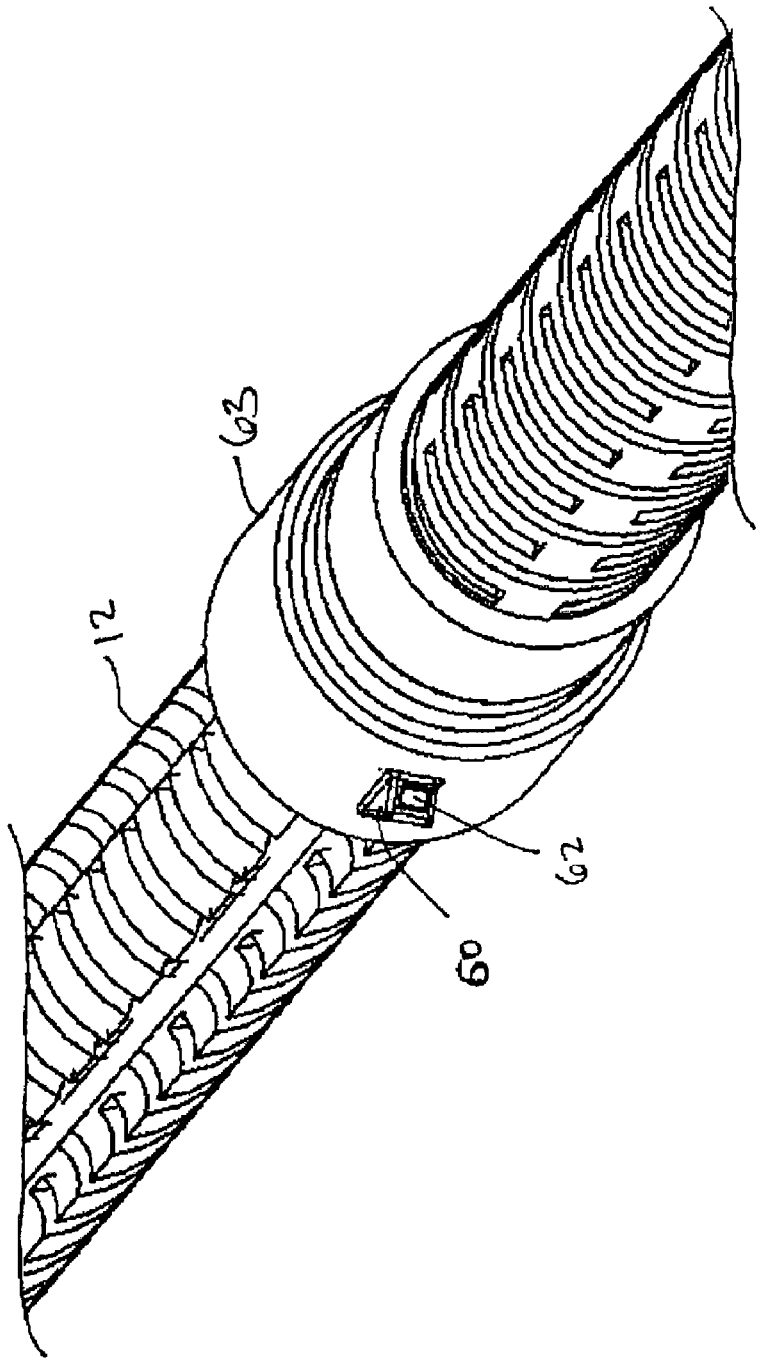
FIG. 10 is a perspective view of a portion of the elongate shaft of the device of FIG. 1A, showing an optical image gathering unit.

The various devices disclosed herein can also include a variety of other features to facilitate use thereof. For example, the device 10 can include an optical image gathering unit disposed on a distal end of the elongate shaft 12, or on the end effector 16, and configured to acquire images during endoscopic procedures. While the location of the unit can vary, FIG. 10 illustrates a ramp-shaped housing 60 that protrudes from an outer surface of a coupling 63 on the elongate shaft 12, and that contains the optical image gathering unit therein. A viewing window 62 is formed on a distal-facing surface of the housing 60 to allow the unit to acquire images of the end effector 16 and surrounding surgical site. The images from the optical image gathering unit can be transferred to an external image display screen, or alternatively the device 10 can include image display screen disposed on or coupled to a proximal portion of the device. FIGS. 9A-9B illustrates one embodiment of an image display screen 70 protruding outward from the handle 14.

The present invention also provides exemplary methods for fastening and optionally cutting tissue. In one exemplary embodiment, the elongate shaft of a surgical stapling and cutting device, such as device 10 of FIG. 1A, can be inserted translumenally, i.e., trans-orally or trans-anally, into a body lumen to position the end effector 16 coupled to the distal end 12b of the elongate shaft 12 adjacent to tissue to be fastened. The end effector 16 can then be manipulated to position tissue to be fastened within the jaws 18, 20, and the knob 50 can be moved as previously described to rotate the end effector 16, close the jaws 18, 20, and fire the staples.

In another embodiment, the various devices disclosed herein, including portions thereof, can be designed to be disposed of after a single use, or they can be designed to be used multiple times. In either case, the device can be reconditioned for reuse after at least one use. Reconditioning can include any combination of the steps of disassembly of the device, followed by cleaning or replacement of particular pieces, and subsequent reassembly. By way of example, the cartridge, including the drive sled, can be removed from the end effector and replaced with a new cartridge containing one or more fasteners therein. The cartridge can also preferably contain a blade formed on the drive sled for cutting fastened tissue. Various other portions of the device can also be removed and replaced. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An endoscopic stapling device, comprising:
   an elongate shaft having proximal and distal ends;
   an end effector coupled to a distal end of the elongate shaft for engaging tissue and delivering at least one fastener to the engaged tissue;
   a handle coupled to a proximal end of the elongate shaft; and
   an actuator operatively coupled to the end effector and the handle, the actuator having a first position in which rotation of the actuator relative to the elongate shaft causes rotation of the end effector about the longitudinal axis of the elongate shaft, and a second position in which rotation of the actuator relative to the elongate shaft causes firing of at least one fastener from the end effector.

2. The device of claim 1, wherein the actuator is adapted to translate along a longitudinal axis of the elongate shaft between the first and second positions, and wherein translation of the actuator from the first position to the second position is effective to close the end effector for engaging tissue.

3. The device of claim 2, wherein the end effector includes opposed jaws for engaging tissue therebetween and the actuator includes a clutch on the distal end thereof, and wherein, when the actuator is translated from the first position to the second position, the clutch is adapted to abut against a cam surface formed on at least one of the jaws to close the jaws.

4. The device of claim 2, wherein the handle includes a translating member that is adapted to translate the actuator between the first and second positions, and a rotatable member that is adapted to rotate the actuator relative to the elongate shaft.

5. The device of claim 1, wherein the actuator comprises a rotatable and translatable drive shaft operatively associated with the handle and the end effector.

6. The device of claim 5, wherein the drive shaft includes a clutch on a distal end thereof 7. The device of claim 6, wherein, when the actuator is in the first position, the clutch is adapted to engage a housing of the end effector such that rotation of the actuator and the clutch is effective to rotate the end effector.

8. The device of claim 6, wherein, when the actuator is in the second position, the clutch is adapted to engage and rotate a gear assembly that advances a driver disposed within the end effector to fire at least one fastener from the end effector.

9. The device of claim 5, wherein at least a portion of the drive shaft is formed from an electroactive polymer material, and wherein the handle is effective to deliver energy to the drive shaft to cause the electroactive polymer material to axially contract and radially expand and thereby translate the drive shaft.

10. The device of claim 1, wherein the end effector includes a cartridge removably disposed therein, the cartridge containing a plurality of staples for stapling tissue and a blade for cutting stapled tissue.

11. The device of claim 1, further comprising an optical image gathering unit disposed on a distal end of the elongate shaft, the optical image gathering unit being adapted to acquire images during endoscopic procedures.

12. The device of claim 11, further comprising an image display screen disposed on a proximal portion of the device and adapted to communicate with the optical image gathering unit to display the acquired images.

13. An endoscopic stapling device, comprising:
   an elongate shaft having an end effector coupled to a distal end thereof, a handle movably coupled to a proximal end thereof, and a drive shaft operatively coupled with the handle and the end effector, wherein rotation of the handle relative to the elongate shaft rotates the end effector about the longitudinal axis of the elongate shaft, closes the end effector to engage tissue, and fires at least one fastener from the end effector.

14. The device of claim 13, wherein the drive shaft is movable between a first position, in which rotation of the drive shaft causes corresponding rotation of the end effector relative to the elongate shaft without closing and firing the end effector, and a second position, in which rotation of the drive shaft causes closing and firing of the end effector without rotating the end effector relative to the elongate shaft.

15. The device of claim 14, wherein the drive shaft is adapted to translate relative to a longitudinal axis of the elongate shaft to move between the first and second positions, and wherein translation of the drive shaft from the first position to the second position is adapted to close opposed jaws of the end effector.

16. The device of claim 14, wherein a distal end of the drive shaft engages a portion of the end effector to rotate the end effector when the drive shaft is in the first position, and wherein a distal end of the drive shaft engages a gear assembly to rotate the gear assembly when the drive shaft is in the second position, rotation of the gear assembly being effective to advance a driver disposed within the end effector to fire at least one fastener from the end effector.

* * * * *